United States Patent [19]

Bison et al.

[11] 4,252,744
[45] Feb. 24, 1981

[54] METHOD OF RACEMIZING OPTICALLY ACTIVE 1-PHENYLETHYLAMINE

[75] Inventors: Günter Bison, Troisdorf-Sieglar; Kurt Breideneichen, Troisdorf; Walter Heinzelmann, Leverkusen; Wolfgang Wolfes, Niederkassel-Mondorf, all of Fed. Rep. of Germany

[73] Assignee: Dynamit Nobel Aktiengesellschaft, Troisdorf, Fed. Rep. of Germany

[21] Appl. No.: 696,337

[22] Filed: Jun. 15, 1976

Related U.S. Application Data

[63] Continuation of Ser. No. 509,161, Sep. 25, 1974, abandoned.

[30] Foreign Application Priority Data

Sep. 28, 1973 [DE] Fed. Rep. of Germany ....... 2348801

[51] Int. Cl.$^3$ ............................................. C07C 85/145
[52] U.S. Cl. ................................................... 564/302
[58] Field of Search ................................. 260/570.8 R

[56] References Cited

U.S. PATENT DOCUMENTS

| | | | |
|---|---|---|---|
| 2,214,034 | 9/1940 | Tabern | 260/570.6 |
| 2,608,583 | 8/1952 | Aschner | 260/570.8 |
| 3,168,566 | 2/1965 | Loter et al. | 260/570.8 |

*Primary Examiner*—Robert V. Hines
*Attorney, Agent, or Firm*—Sprung, Felfe, Horn, Lynch & Kramer

[57] ABSTRACT

A process for the preparation of racemic phenylethylamine which comprises contacting an optical antipode therefore, e.g., L(−) or D(+)-1-phenylethylamine with sodium amide or sodium hydride.

1 Claim, No Drawings

METHOD OF RACEMIZING OPTICALLY ACTIVE 1-PHENYLETHYLAMINE

This is a continuation of application Ser. No. 509,161, filed Sept. 25, 1974 and now abandoned.

BACKGROUND OF THE INVENTION

1. Field of the Invention

This invention relates to the preparation of racemic 1-phenylethylamine. More particularly, this invention is directed to the economic use of an optically active antipode of phenylethylamine and to a simple process for converting the same to the racemate whereby through resolution thereof the other optically active form can be readily prepared. This invention is particularly directed to the racemization of phenylethylamine by contacting an optically active form thereof with sodium amide or sodium hydride.

2. Discussion of the Prior Art

The antipodes of 1-phenylethylamine are being used increasingly as resolving bases for racemization since phenylethylamine is synthesizable and can readily be resolved into its antipodes. In contrast to naturally occurring alkaloids the optically active forms of 1-phenylethylamine can be provided in any desired amount for technical purposes.

In the racemization of synthetically prepared resolving bases, two antipodes are necessarily produced in equal amounts. However, it is largely only one resolving base that is needed for the racemization so that the other antipode is not needed at all. It is therefore necessary to re-racemize the antipodes of 1-phenylethylamine which are usually the necessary result of its production and to recycle them to the resolving process.

The racemization of optically active isomers is generally known. It is especially easy to racemize compounds which are capable of transformation to the enol form. Such substances have an activated hydrogen atom adjacent to the carbonyl group. By heating the substance or by warming it in the presence of an alkali or an acid such optically active compound can easily be transformed to the racemate.

Optically active forms of 1-phenylethylamine, however, do not have the structural characteristics of those optically active isomers which can readily be racemized, i.e., they do not have an activated hydrogen atom adjacent to a carbonyl group. In view of this chemical feature thereof the racemization of an optically active form of 1-phenylethylamine is particularly difficult. It has no electronegative substituents such as an aldehyde, ketone, acid or ester group, for example, which might give mobility to the hydrogen atom adjacent a carbonyl group.

In U.S. Pat. No. 3,168,566 there is described a process for the racemization of optically active antipodes which are difficult to transform into the racemate. There is particularly described therein a process for racemization of α-phenylamine and α-naphthylamine. In the process described the optically active amines are racemized by heating them, in substance, under an inert gas or in a diluent in the presence of an alkali metal. To achieve as complete a racemization as possible, the substance is heated up to about 200° C. The best results are achieved with the addition of metallic sodium. Other additives are mentioned in the patent, notably aluminum isopropylate and sodium ethylate. These have proven to have little or no activity.

The process described in U.S. Pat. No. 3,168,566 suffers from some important disadvantages. Even on a laboratory scale a shift to larger units of volume than those specified in the patent results in a longer detention of the metallic sodium in the reaction mixture, i.e., heating time is increased, reaction time is increased and cooling time is increased. The result of this longer detention of metallic sodium in the reaction mixture is a decomposition of the amine due to the aggressiveness of the alkali metal. Consequently, great losses of yield result as shown in the comparative example below.

It has, therefore, become desirable to provide a process for the racemization of optically active forms of 1-phenylethylamine by a process which can be carried out on a large commerical scale. It has become particularly desirable to provide such a process which does not require the use of an alkali metal which always presents difficulty in handling. It has become desirable to provide a simple process which utilizes readily available common chemicals and which provides high yields of the desired racemate.

SUMMARY OF THE INVENTION

The objects of this invention are provided by a process for preparing racemic 1-phenylethylamine which process comprises contacting L(−)-1-phenylethylamine or D(+)-1-phenylethylamine with sodium amide or sodium hydride.

In accordance with the present invention it has been discovered that simply by contacting an optically active form of 1-phenylethylamine with sodium amide and/or sodium hydride that the racemate thereof can be prepared. Generally speaking, the sodium amide and/or sodium hydride is used in an amount between 0.01 weight percent and 10 weight percent, based upon the amount of optically active form of 1-phenylethylamine undergoing racemization. The process is carried out with an inert atmosphere at temperatures of 70° to 150° C.

The time during which the 1-phenylethylamine is in the presence of sodium amide is not critical at racemization temperatures of 70° to 150° C. and such time can be as long as 24 hours. Preferably the process is carried out for a period of between 5 and 15 minutes. The short transformation time permits the process to be carried out in a continuous manner in a pass-through heater.

It was quite surprising under the circumstances to find that sodium amide and/or sodium hydride would perform a racemization function for an optically active 1-phenylethylamine, particularly since it had long been considered that compounds such as these would be inactive when compared with metallic sodium. Naturally, one of skill in the art believed that the metallic sodium possessed far greater activity for such racemization and, indeed, such a minimum reactivity provided by the metallic sodium would be required. To find that the lesser reactive compounds, sodium amide and sodium hydride, provide such racemization was considered to be quite surprising.

The method of the present invention offers a number of advantages over the processes of the state of the art. For example, racemization can be performed in relatively large volume units and only traces of ammonia are produced due to decomposition of the amine. In contrast to the process of U.S. Pat. No. 3,168,566 substantially higher yields are provided thus permitting racemization of the antipodes of 1-phenylethylamine on an industrial scale.

If the racemizing agent is sodium hydride it is perferred that the sodium hydride be used in the form of an oil dispersion as such facilitates the handling of the sodium hydride.

In either case the amount of sodium amide or sodium hydride used is between 0.01 and 10% by weight, based upon the weight of the optically active form of 1-phenylethylamine. Preferably, the sodium amide or sodium hydride is used in a quantity of 0.01 to 1% by weight of the charge optically active 1-phenylethylamine.

While racemization can be effected at temperatures of 70° to 150° C., temperatures of 100° to 140° C. are preferred. These temperatures are considerably lower than the temperatures which must be used in the optimum practice of the process of U.S. Pat. No. 3,168,566. Thus, while the temperature ranges of U.S. Pat. No. 3,168,566 and the within process may overlap in principal, lesser temperatures are required in the preferred mode of practice of the present invention than are required in the optimization of the process of U.S. Pat. No. 3,168,566.

Another advantage of the present invention resides in the fact that racemization can take place in a relatively short time. In the case of the laboratory scale batches racemization is completed in about 5 minutes. An indication of the end of racemization is the change of color of the hot solution from yellow to purple red, the color of the racemate.

It is advantageous, in the practice of the present invention, to utilize the sodium amide in a powder form, preferably a powder form where the average particle size is less than 30 microns in diameter.

In order to more fully illustrate the nature of the invention and the manner of practicing the same the following examples are presented.

EXAMPLE 1

In a flask having a capacity of 250 ml and provided with a stirrer, a thermometer, a reflux condenser and a nitrogen gas feed tube, 50 g of D(+)-1-phenylethylamine having a specific rotation $[\alpha]_D^{20} = +39.9°$ ($D_4^{20}=0.95$) was heated to 130° C. with stirring, under a nitrogen atmosphere, in the presence of 500 mg of powdered sodium amide. Approximately 10 minutes after the temperature was reached the color of the reaction solution changed from its original yellow to red-violet. A specimen of the substance, taken for determination of the optical rotation, already showed a 100% racemization. The reaction solution was then cooled within 1 hour to room temperature, the sodium amide was decomposed with 2 ml of ethanol, and the product was refined by distillation.

At $BP_{11}=71°-71.5°$ C. a main fraction of 47 g (=94% of the theory) of 1-phenylethylamine was obtained.

$[\alpha]_D^{20} = \pm 0°$; $n_D^2 = 1.5266$

EXAMPLE 2

2000 g of L(−)-1-phenylethylamine having a rotation $[\alpha]_D^{20} = -39.9°$ ($D_4^{20}=0.95$) and 10 g of powdered sodium amide were placed in an automatic stirring flask with a capacity of 4 liters, provided with a thermometer, a tube for feeding nitrogen, and a reflux condenser. The reflux condenser was connected to a receiver containing 1N hydrochloric acid serving to capture the ammonia that developed.

The reaction mixture was heated within 30 minutes to 130° C. Upon reaching this temperature, the solution changed from yellow to purple-red. It was stirred for an additional 10 minutes at this temperature. A specimen taken at this moment showed no optical activity. The reaction mixture was cooled over a period of 4 hours down to room temperature with nitrogen shielding. When a temperature of about 60° C. was reached, 16.5 ml of ethanol was added so as to destroy the sodium amide.

By distillative refinement, a main fraction was obtained at $BP_{13}=73.5°$ to 75° C. of 1.910 g (=95.5% of the theory) of 1-phenylethylamine:

$[\alpha]_D^{20} = \pm 0°$ $n_D^{20} = 1.5267$

The back titration of the hydrochloric acid from the receiver showed, allowing for the destroyed sodium amide, that only 37.2 g (1=1.87%) of 1-phenylethylamine was decomposed through formation of ammonia.

EXAMPLE 3

2000 g of L(−)-1-phenylethylamine having a rotation $[\alpha]_D^{20}=40.1°$ ($D_4^{20}=0.95$) was treated with 12.5 g of a mixture of sodium hydride and oil (=80 weight percent NaH) as in Example 2. The reaction mixture was completely racemized. By distillation at $BP_{12}=71.5°-73°$ C. 1472.0 g (=73.6%) 1-phenylethylamine $[\alpha]_D^{20}=\pm 0°$ was obtained. The distillation residue amounted to 420.0 g (=21.0%).

COMPARATIVE EXAMPLE 50.0 g of L(−)-1-phenylethylamine with a specific rotation of $[\alpha]_D^{20}=39.9°$ ($D_4^{20}=0.950$) was treated under a nitrogen atmosphere with 0.125 g of metallic sodium and heated for 30 minutes at 185° C. with intense stirring. The color of the solution served as the indication as to whether racemization had taken place. The solution of the enantiomer was pale yellow when hot. The racemate would have a purple-red color. Since after 60 minutes of stirring at 185° C. the yellowish reaction solution did not undergo an intense change of color, a specimen was taken and the optical rotation thereof was measured. The rotation was quite the same as that of the starting material.

An additional 0.125 g of metallic sodium was then added. After 10 minutes the reaction solution changed color from the original yellow to purple-red. The specimen taken at this time showed complete racemization, upon analysis. The reaction mixture was cooled and the delivery of nitrogen was continued in order to transfer any remaining traces of ammonia to the receiver filled with hydrochloric acid.

Distillative refinement of the raw product yielded 17.2 g (34.4% of theory) of a principal fraction having the following physical characteristics:

$B.P._{11} 71°-74°$ C.

$n_D^{20} = 1.5260$ $[\alpha]_D^{20} = \pm 0°$

These data show that the principal fraction consisted of racemic 1-phenylethylamine. 20.4 g remained as residue (52.3% of the theory). The hydrochloric acid in the receiver was back titrated. Since during the racemization the phenylethylamine decomposed to yield ammonia, the back titrated provided an indication of the degree of decomposition. The titration showed that 17.0 g (34% of theory) decomposed to yield ammonia.

What is claimed is:

1. A process for preparing racemic 1-phenylethylamine which comprises contacting L(−)-1-phenylethylamine or D(+)-1-phenylethylamine with 0.01 to 1 weight percent, based on the amount of said phenylethylamine, of sodium amide or sodium hydride at a temperature of 70° to 150° C. for a period of time between 5 and 15 minutes.

* * * * *